US00PP22371P2

(12) United States Plant Patent
Eveleens

(10) Patent No.: US PP22,371 P2
(45) Date of Patent: Dec. 20, 2011

(54) CARNATION PLANT NAMED 'HILCATI'

(50) Latin Name: *Dianthus caryophyllus*
Varietal Denomination: Hilcati

(75) Inventor: Peter Eveleens, Aalsmeer (NL)

(73) Assignee: Hilverda Kooij B.V., De Kwakel (NL)

( * ) Notice: Subject to any disclaimer, the term of this patent is extended or adjusted under 35 U.S.C. 154(b) by 0 days.

(21) Appl. No.: 12/924,021

(22) Filed: Sep. 17, 2010

(51) Int. Cl.
*A01H 5/00* (2006.01)

(52) U.S. Cl. ..... Plt./283

(58) Field of Classification Search ..... Plt./283
See application file for complete search history.

*Primary Examiner* — Annette Para
(74) *Attorney, Agent, or Firm* — C. A. Whealy

(57) ABSTRACT

A new and distinct cultivar of Carnation plant named 'Hilcati', characterized by its compact, upright, somewhat outwardly spreading and mounded plant habit; freely branching habit; freely flowering habit; large double red-colored flowers that are positioned above and beyond the foliar plane on strong peduncles; and good garden performance.

1 Drawing Sheet

Botanical designation: *Dianthus caryophyllus.*
Cultivar denomination: 'HILCATI'.

BACKGROUND OF THE INVENTION

The present invention relates to a new and distinct cultivar of Carnation plant, botanically known as *Dianthus caryophyllus*, grown commercially as a potted plant and hereinafter referred to by the name 'Hilcati'.

The new Carnation plant is a product of a planned breeding program conducted by the Inventor in Aalsmeer, The Netherlands. The objective of the breeding program was to develop new freely-branching Carnation plants with numerous attractive flowers.

The new Carnation plant originated from a cross-pollination made by the Inventor in May, 2007 of a proprietary selection of *Dianthus caryophyllus* identified as code number A 565254-01, not patented, as the female, or seed, parent with a proprietary selection of *Dianthus caryophyllus* identified as code number A 26270-01, not patented, as the male, or pollen, parent. The new Carnation plant was discovered and selected by the Inventor as a single flowering plant within the progeny of the stated cross-pollination in a controlled greenhouse environment in Aalsmeer, The Netherlands in July, 2008.

Asexual reproduction of the new Carnation plant by terminal cuttings propagated in a controlled greenhouse environment in Aalsmeer, The Netherlands since 2008, has shown that the unique features of this new Carnation plant are stable and reproduced true to type in successive generations of asexual reproduction.

SUMMARY OF THE INVENTION

Plants of the new Carnation have not been observed under all possible environmental conditions. The phenotype may vary somewhat with variations in environment such as temperature and light intensity, without, however, any variance in genotype.

The following traits have been repeatedly observed and are determined to be the unique characteristics of 'Hilcati'. These characteristics in combination distinguish 'Hilcati' as a new and distinct cultivar of Carnation plant:

1. Compact, upright, somewhat outwardly spreading and mounded plant habit.

2. Freely branching habit.
3. Freely flowering habit.
4. Large double red-colored flowers that are positioned above and beyond the foliar plane on strong peduncles.
5. Good garden performance.

Plants of the new Carnation differ from plants of the female parent selection in the following characteristics:

1. Plants of the new Carnation are more freely flowering than plants of the female parent selection.
2. Flower petals of plants of the new Carnation are more rounded in shape than flower petals of plants of the female parent selection.
3. Flowers of plants of the new Carnation are darker red in color than flowers of plants of the female parent selection.

Plants of the new Carnation differ from plants of the male parent selection in the following characteristics:

1. Plants of the new Carnation are more freely flowering than plants of the male parent selection.
2. Plants of the new Carnation have larger flowers than plants of the male parent selection.
3. Flowers of plants of the new Carnation are darker red in color than flowers of plants of the male parent selection.
4. Plants of the new Carnation have shorter peduncles than plants of the male parent selection.

Plants of the new Carnation can be compared to plants of the Carnation 'Napoli', not patented. In side-by-side comparisons conducted in Aalsmeer, The Netherlands, plants of the new Carnation differed from plants of 'Napoli' in the following characteristics:

1. Flower petals of plants of the new Carnation were not as rounded as flower petals of plants of 'Napoli'.
2. Flower petals of plants of the new Carnation were more emarginate than flower petals of plants of 'Napoli'.
3. Flowers of plants of the new Carnation were lighter red in color than flowers of plants of 'Napoli'.

BRIEF DESCRIPTION OF THE PHOTOGRAPH

The accompanying photograph illustrates the overall appearance of the new Carnation plant showing the colors as true as it is reasonably possible to obtain in colored reproductions of this type. Colors in the photograph may differ slightly from the color values cited in the detailed botanical description which accurately describe the colors of the new Carnation plant. The photograph comprises a side perspective view of a typical flowering plant of 'Hilcati' grown in a container.

DETAILED BOTANICAL DESCRIPTION

Plants used in the aforementioned photograph and following observations and measurements describe plants grown during the summer in 10.5-cm containers in a glass-covered greenhouse in Aalsmeer, The Netherlands and under conditions and practices which approximate those generally used in commercial potted Carnation production. During the production of the plants, day temperatures ranged from 20° C. to 25° C. and night temperatures ranged from 16° C. to 22° C. Plants were pinched one time four weeks after planting. Plants were three months old when the photograph and the detailed description were taken. In the following description, color references are made to The Royal Horticultural Society Colour Chart, 2007 Edition, except where general terms of ordinary dictionary significance are used.

Botanical classification: *Dianthus caryophyllus* 'Hilcati'.

Parentage:

*Female, or seed, parent.*—Proprietary selection of *Dianthus caryophyllus* identified as code number A 565254-01, not patented.

*Male, or pollen, parent.*—Proprietary selection of *Dianthus caryophyllus* identified as code number A 26270-01, not patented.

Propagation:

*Type.*—By terminal cuttings.

*Time to initiate roots, summer.*—About six days at 20° C. to 25° C.

*Time to initiate roots, winter.*—About eight days at 18° C.

*Time to produce a rooted young plant, summer.*—About three weeks at 20° C. to 25° C.

*Time to produce a rooted young plant, winter.*—About five weeks at 18° C.

*Root description.*—Medium in thickness, fibrous; white in color.

*Rooting habit.*—Moderate branching; medium in density.

Plant description:

*Plant form.*—Compact, upright, somewhat outwardly spreading and mounded plant habit; narrow inverted triangle.

*Branching habit.*—Freely-branching growth habit; when pinched, about seven lateral branches develop; dense and bushy growth habit.

*Plant height.*—About 16.5 cm.

*Plant diameter or spread.*—About 18.7 cm.

*Lateral branches.*—Length: About 11.6 cm. Diameter: About 3 mm. Internode length: About 2.1 cm. Strength: Strong. Texture: Smooth, glabrous. Color: Close to 136B and 137A.

Foliage description:

*Arrangement.*—Opposite, simple; sessile.

*Length.*—About 8.4 cm.

*Width.*—About 9 mm.

*Shape.*—Narrowly oblanceolate.

*Apex.*—Acute.

*Base.*—Attenuate.

*Margin.*—Entire.

*Texture, upper and lower surfaces.*—Smooth, glabrous.

*Venation pattern.*—Parallel.

*Color.*—Developing leaves, upper surface: Close to 137A to 137B; towards the base, close to 143C. Developing leaves, lower surface: Close to 137C; towards the base, close to 143C. Fully expanded leaves, upper surface: Close to N137C; venation, close to N137C. Fully expanded leaves, lower surface: Close to N137C; venation, close to 143A.

Flower description:

*Flower type and habit.*—Large double flowers; flowers terminal and axillary, either solitary or in clusters of three; freely flowering habit with typically about 35 flowers developing per plant; flowers positioned above and beyond the foliar plane on strong peduncles; flowers face mostly upright.

*Fragrance.*—Flowers moderately fragrant; sweet, clove-like.

*Natural flowering season.*—Flowering is continuous through the summer and late summer in The Netherlands; plants begin flowering about 13 weeks after planting.

*Flower longevity.*—Flowers last about ten days on the plant; flowers not persistent.

*Flower diameter.*—About 4.9 cm.

*Flower depth.*—About 4 cm.

*Flower buds.*—Length: About 1.7 cm. Diameter: About 9 mm. Shape: Obovate. Color: Close to 137A to 137B; towards the base, close to 143B.

*Petals/petaloids.*—Quantity/arrangement: About 32 per flower arranged in several whorls. Length, outer petals: About 3.8 cm. Width, outer petals: About 1.8 cm. Shape: Roughly spatulate. Apex: Praemorse. Base: Acute. Margin: Entire. Texture, upper and lower surfaces: Smooth, glabrous; velvety. Color: When opening, upper surface: Close to 45B; towards the base, close to 145C to 145D. When opening, lower surface: Close to 51B to 51C; towards the base, close to 145C to 145D. Fully opened, upper surface: Close to 47B; towards the base, close to 145C to 145D. Fully opened, lower surface: Close to 55B; towards the base, close to 145C to 145D.

*Sepals.*—Quantity/arrangement: Five fused in a single whorl. Length: About 2 cm. Width: About 6 mm. Shape: Oblong. Apex: Broadly acute. Margin: Entire. Texture, upper and lower surfaces: Smooth, glabrous. Color, upper surface: Close to 147C to 147D. Color, lower surface: Close to 137A.

*Peduncles.*—Length: About 1.6 cm. Diameter: About 2 mm. Strength: Strong. Texture: Smooth, glabrous. Color: Close to 136B and 137A.

*Reproductive organs.*—Stamens: None observed. Pistils: Quantity: About two per flower. Pistil length: About 2.6 cm. Stigma shape: Club-shaped. Stigma color: Close to 55A. Style length: About 2.5 cm. Style color: Close to 55B to 55D; towards the base, close to NN155C. Ovary color: Close to 150C to 150D. Fruits/seeds: Fruit and seed development have not been observed on plants of the new Carnation.

Disease/pest resistance: Plants of the new Carnation have not been observed to be resistant to pathogens and pests common to Carnations.

Garden performance: Plants of the new Carnation have been observed to have good garden performance and to tolerate wind, rain and temperatures ranging from about 5° C. to 35° C.

It is claimed:

1. A new and distinct Carnation plant named 'Hilcati' as illustrated and described.

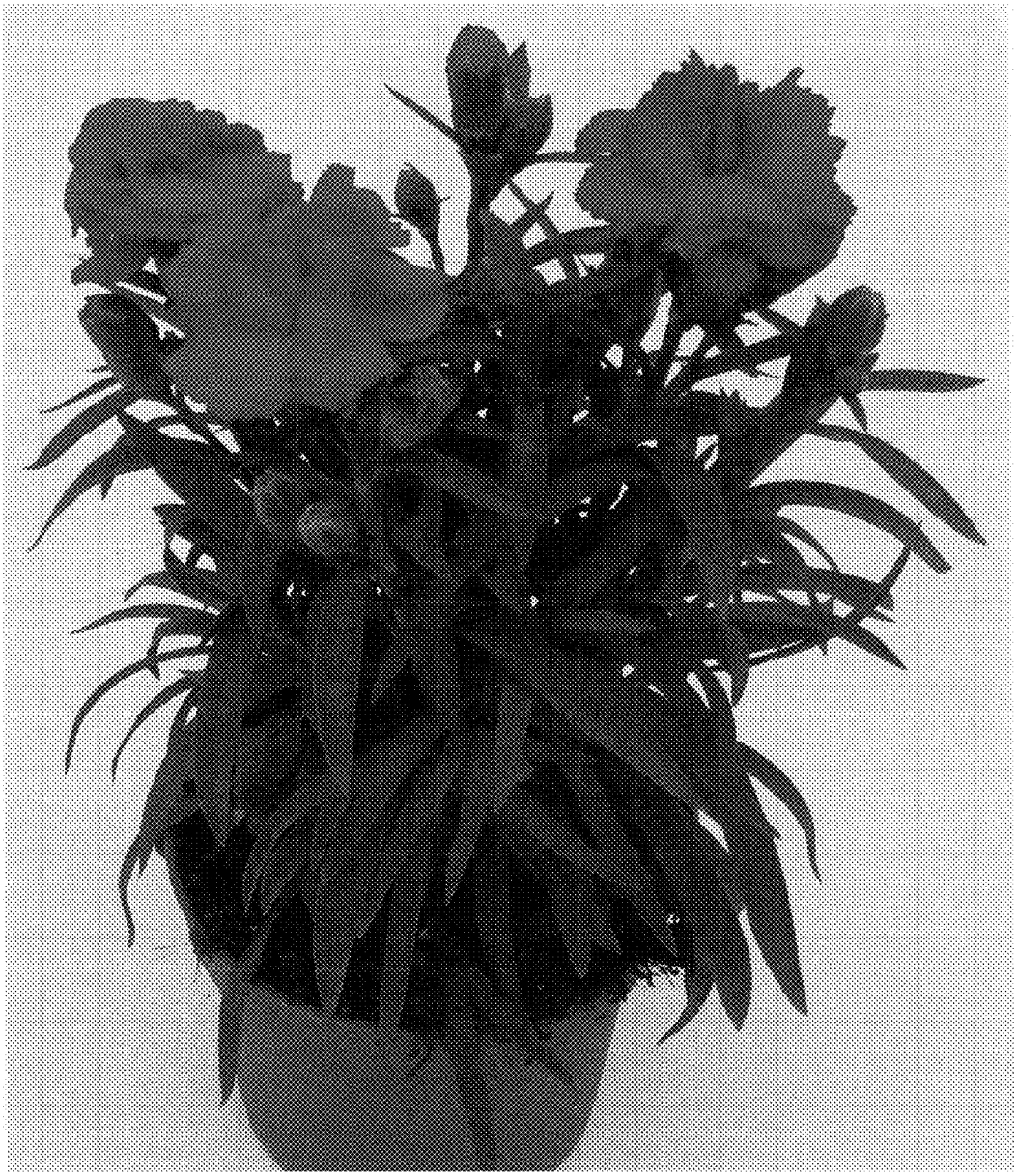

* * * * *